United States Patent
Okubayashi et al.

(10) Patent No.: US 8,476,338 B2
(45) Date of Patent: Jul. 2, 2013

(54) DENTAL CURABLE COMPOSITION AND COMPOSITE RESIN USING THE SAME

(75) Inventors: Masaki Okubayashi, Kurashiki (JP); Hirotaka Kita, Kurashiki (JP); Yusuke Takahata, Kurashiki (JP); Akiko Ota, Kurashiki (JP)

(73) Assignee: Kuraray Noritake Dental Inc., Kurashiki-shi (JP)

( * ) Notice: Subject to any disclaimer, the term of this patent is extended or adjusted under 35 U.S.C. 154(b) by 161 days.

(21) Appl. No.: 13/141,381

(22) PCT Filed: Dec. 10, 2010

(86) PCT No.: PCT/JP2010/007203
§ 371 (c)(1),
(2), (4) Date: Jun. 22, 2011

(87) PCT Pub. No.: WO2011/074222
PCT Pub. Date: Jun. 23, 2011

(65) Prior Publication Data
US 2011/0257292 A1    Oct. 20, 2011

(30) Foreign Application Priority Data
Dec. 18, 2009   (JP) ................. 2009-288115

(51) Int. Cl.
*A61K 6/083* (2006.01)
*A61C 5/00* (2006.01)

(52) U.S. Cl.
USPC .............................. 523/116; 433/215; 106/35

(58) Field of Classification Search
CPC ........................... A61K 6/0005; A61K 6/0008
USPC ............................ 523/116; 433/215; 106/35
See application file for complete search history.

(56) References Cited

U.S. PATENT DOCUMENTS

| | | | |
|---|---|---|---|
| 4,719,297 A | 1/1988 | Henne et al. | |
| 5,795,497 A | 8/1998 | Kimura et al. | |
| 6,933,327 B2 | 8/2005 | Yamakawa et al. | |
| 7,393,882 B2 | 7/2008 | Wu et al. | |
| 2011/0003267 A1 | 1/2011 | Terakawa et al. | |
| 2011/0046260 A1* | 2/2011 | Okubayashi et al. | 523/115 |
| 2011/0065828 A1 | 3/2011 | Okubayashi et al. | |

FOREIGN PATENT DOCUMENTS

| | | | |
|---|---|---|---|
| EP | 0 009 348 | | 4/1980 |
| JP | 57 197289 | | 12/1982 |
| JP | 9 255516 | | 9/1997 |
| JP | 09-169613 A | * | 12/1997 |
| JP | 10 1473 | | 1/1998 |
| JP | 11 92461 | | 4/1999 |
| JP | 2000 159621 | | 6/2000 |
| JP | 2002 138008 | | 5/2002 |
| JP | 2005 517688 | | 6/2005 |
| JP | 2007 302631 | | 11/2007 |
| WO | 2008 096753 | | 8/2008 |
| WO | 2009 133911 | | 11/2009 |

OTHER PUBLICATIONS

International Search Report issued Mar. 15, 2011 in PCT/JP10/07203 filed Dec. 10, 2010.

\* cited by examiner

*Primary Examiner* — Tae H Yoon
(74) *Attorney, Agent, or Firm* — Oblon, Spivak, McClelland, Maier & Neustadt, L.L.P.

(57) ABSTRACT

The present invention provides a dental curable composition exhibiting both excellent light diffusion and excellent transparency, and having high mechanical strength and surface smoothness and gloss after polishing as a cured product as well as good handling properties as a paste. The present invention is a dental curable composition including: a polymerizable monomer (A) having a refractive index of 1.52 to 1.58 after polymerization; inorganic particles (B) having a refractive index of 1.43 to 1.50; and inorganic particles (C) having a refractive index of 1.52 to 1.58. The inorganic particles (B) are aggregates of inorganic fine particles having an average primary particle size of 2 to 50 nm, and the content of the inorganic particles (B) is 0.1 to 10% by weight.

16 Claims, No Drawings

DENTAL CURABLE COMPOSITION AND COMPOSITE RESIN USING THE SAME

This application is a 371 of PCT/JP2010/007203 filed Dec. 10, 2010. Priority to Japanese patent application 2009-288115, filed Dec. 18, 2009, is claimed.

TECHNICAL FIELD

The present invention relates to a dental curable composition that can be used suitably as a dental material, particularly a dental composite resin, that can be used as a substitute for a part of a natural tooth or an entire natural tooth in the field of dental treatment.

BACKGROUND ART

A dental curable composition containing a polymerizable monomer, a filler, and a polymerization initiator is called a composite resin, and this dental material is most widely used today as a restorative material for repairing fractures of teeth and dental caries. Such a dental curable composition is required to have the following properties. Specifically, as a cured product obtained after polymerization curing, the dental curable composition is required to have sufficient mechanical strength and hardness to serve as a substitute for natural teeth, wear resistance to biting pressure in an oral cavity, surface smoothness and gloss, etc. Furthermore, as a paste which has not yet been polymerized and cured, the dental curable composition is expected to offer ease of handling (or to have excellent handling properties) for dental clinicians and technicians, for example, proper fluidity and forming property, no adhesion to dental instruments, no stickiness, etc.

These properties of the dental curable composition are greatly influenced by the material, shape, particle size, and content of a filler used therein and by the combination of fillers used together. For example, when an inorganic filler having an average particle size of more than 1 μm is used, the filling rate of the filler in the polymerizable monomer can be increased easily and therefore sufficient mechanical strength as a cured product and excellent handling properties as a paste can be obtained. The use of such an inorganic filler has, however, a drawback in that it is difficult to obtain satisfactory gloss even after final polishing, and even if satisfactory gloss is obtained, the gloss cannot be retained for a long time. On the other hand, when an inorganic ultrafine particle filler having an average particle size of 1 μm or less is used, the surface smoothness and gloss after polishing of the cured product and the gloss durability in the oral cavity are improved. The use of such an inorganic ultrafine particle filler has, however, a drawback in that when the inorganic filler is mixed and kneaded with the polymerizable monomer, the viscosity of the resulting paste increases significantly, which makes it difficult to increase the content of the filler. As a result, the mechanical strength of the cured product decreases, and the unpolymerized pasty composition becomes sticky, which reduces the handling properties. Under these circumstances, it is difficult to increase the mechanical strength and the surface smoothness and gloss after polishing of the cured product and the handling properties of the paste in a balanced manner.

On the other hand, dental curable compositions are required not only to have the above-mentioned properties but also to match natural teeth, that is, to have optical properties such as color, transparency, and light diffusion similar to those of natural teeth. Particularly in recent years, there has been a demand for dental curable compositions having optical properties similar to those of dentin or optical properties similar to those of enamel so that they can match respective parts of a tooth to be restored. In other words, dental curable compositions having different colors, transparencies, and light diffusions are expected to be used for different parts. It is possible to adjust the color and transparency by adjusting the content of a pigment, but it is difficult to adjust the light diffusion only by adjusting the content of the pigment.

Patent Literature 1 describes a dental paste containing at least 55% by weight in total of porous, non-pyrogenic silica and non-aggregated primary silica particles having an average diameter of at most about 200 nm. More specifically, one example discloses a dental paste containing, as fillers, non-aggregated silica particles having an average particle size of about 75 nm and aggregated non-pyrogenic silica obtained by spray-drying silica sol having an average particle size of about 75 nm to aggregate the particles.

Patent Literature 2 describes a dental composite material containing a polymerizable monomer, one kind of filler, and another kind of filler. The former filler is obtained by aggregating inorganic filler particles having an average particle size of 0.01 to 1 μm and subjecting the resulting aggregated particles to heat treatment so that the primary particles are loosely bonded with each other, and has a refractive index difference of 0.06 or less from the cured polymerizable monomer. The latter filler has a refractive index difference of more than 0.06 from the cured polymerizable monomer, and has an average particle size of 1 μm or more. This dental composite material has a degree of diffusion D of 0.002 to 0.3, when it is represented by the following formula (1):

$$D=(I_{20}/\cos 20°+I_{70}/\cos 70°/(2I_0) \tag{1}$$

where I denotes the intensity of transmitted light through a sample, and $I_0$, $I_{20}$ and $I_{70}$ denote the intensities of the transmitted light measured at angles of 0, 20, and 70 degrees respectively with respect to the direction perpendicular to the sample plate (the incident direction of the light). One example of Patent Literature 2 discloses a dental composite material containing a polymerizable monomer, one kind of filler, and another kind of filler. The former filler is obtained by aggregating barium boroaluminosilicate glass having an average particle size of 0.7 μm and calcining the resulting aggregated particles so that the primary particles are loosely bonded with each other, and has a refractive index of 1.55. The latter filler is obtained by aggregating spherical silica having an average particle size of 0.2 μm and calcining the resulting aggregated particles.

Patent Literature 3 describes a dental curable composition containing a polymerizable monomer, and an organic-inorganic composite filler having a refractive index difference of 0.01 or more as an absolute value from the cured polymerizable monomer and having an average particle size of 1 to 20 μm. In this dental curable composition, the degree of diffusion D represented by the above formula (1) has a value of 0.01 or more.

CITATION LIST

| | |
|---|---|
| Patent Literature 1 | JP 2005-517688 T |
| Patent Literature 2 | JP 09(1997)-255516 A |
| Patent Literature 3 | JP 2002-138008 A |

SUMMARY OF INVENTION

Technical Problem

The dental paste described in Patent Literature 1 uses non-aggregated silica particles and aggregated porous, non-pyrogenic silica particles obtained by spray-drying silica particles to aggregate them. However, this dental paste does not use particles made of materials with different refractive indices together, and it cannot achieve a good balance between satisfactory light diffusion and transparency.

The dental composite material described in Patent Literature 2 uses silica particles having an average particle size of 0.2 μm as primary particles, which makes it difficult to achieve both a high transparency and a high degree of diffusion. Furthermore, in the filler of barium boroaluminosilicate glass, the primary particles are loosely bonded with each other, which makes it difficult to stably produce a dental composite material having certain level of paste properties. In addition, since the paste properties deteriorate with time, this dental composite material is not necessarily easy to handle and has room for improvement.

The dental curable composition described in Patent Literature 3 uses an organic-inorganic composite filler having a refractive index difference of 0.01 or more from the cured polymerizable monomer and having an average particle size of 1 to 20 μm, and the use of this filler provides handling properties to the paste composition and surface smoothness and gloss after polishing and light diffusion to the cured product. The use of the organic-inorganic composite filler, however, reduces the content of the inorganic filler in the cured product, and leads to the weak bond between the organic-inorganic composite filler and the polymerizable monomer as a matrix. As a result, this dental curable composition cannot have sufficient mechanical strength and has room for improvement.

The present invention has been made in order to solve the above conventional problems, and it is an object of the present invention to provide a dental curable composition exhibiting both excellent light diffusion and excellent transparency, and having excellent mechanical strength and surface smoothness and gloss after polishing as a cured product as well as good handling properties as a paste. It is another object of the present invention to provide a composite resin exhibiting both excellent light diffusion and excellent transparency, and having excellent mechanical strength and surface smoothness and gloss after polishing as a cured product as well as good handling properties as a paste.

Solution to Problem

The present invention is a dental curable composition including: a polymerizable monomer (A) having a refractive index of 1.52 to 1.58 after polymerization; inorganic particles (B) having a refractive index of 1.43 to 1.50; and inorganic particles (C) having a refractive index of 1.52 to 1.58. The inorganic particles (B) are aggregates of inorganic fine particles having an average primary particle size of 2 to 50 nm, and the content of the inorganic particles (B) is 0.1 to 10% by weight.

In the present invention, it is preferable that the inorganic particles (B) have an average particle size of 1.0 to 20 μm. It is preferable that the inorganic particles (B) have a specific surface area of 50 to 400 $m^2/g$ and a pore volume of 0.05 to 1.5 mL/g.

In the present invention, it is preferable that the inorganic particles (C) include non-aggregated inorganic particles (C-I) having an average particle size of 0.1 to 1.0 μm. It is preferable that the inorganic particles (C) include: the non-aggregated inorganic particles (C-I) having the average particle size of 0.1 to 1.0 μm; and aggregated inorganic particles (C-II) having an average particle size of 1 to 20 μm and including silica-based fine particles having an average particle size of 2 to 50 nm and an oxide containing at least one heavy metal, and that a weight ratio between the inorganic particles (C-I) and the inorganic particles (C-II) be 1:4 to 4:1.

In the present invention, it is preferable that a difference between the refractive index of the polymerizable monomer (A) after polymerization and the refractive index of the inorganic particles (C) be 0.03 or less. It is preferable that a difference between the refractive index of the polymerizable monomer (A) after polymerization and the refractive index of the inorganic particles (B) be 0.05 or more.

Preferably, the dental curable composition of the present invention contains 8 to 40% by weight of the polymerizable monomer (A), 0.1 to 10% by weight of the inorganic particles (B), and 59.9 to 91.9% by weight of the inorganic particles (C). In one embodiment, the dental curable composition of the present invention further includes 1 to 10% by weight of inorganic ultrafine particles (D) having an average particle size of 5 to 50 nm.

The present invention is also a composite resin using the dental curable composition described above.

Advantageous Effects of Invention

According to the dental curable composition of the present invention, a cured product having both good light diffusion and high transparency can be obtained. In addition, the cured product also has high surface smoothness and gloss after polishing and high gloss durability, and therefore, the dental curable composition of the present invention offers a good aesthetic appearance. According to the dental curable composition of the present invention, a cured product having high mechanical strength can be obtained. Furthermore, the dental curable composition of the present invention has, as a paste, good handling properties and proper fluidity and forming property. The adhesion to dental instruments and stickiness of the dental curable composition are reduced, and the deterioration with time of the dental curable composition is suppressed. That is, this composition is very easy to handle. The dental curable composition of the present invention can be used particularly suitably as a composite resin, and this composite resin exhibits both excellent light diffusion and excellent transparency, and has excellent mechanical strength and surface smoothness and gloss after polishing as a cured product as well as good handling properties as a paste.

DESCRIPTION OF EMBODIMENTS

Polymerizable Monomer (A)

As the polymerizable monomer (A) used in the present invention, a known polymerizable monomer can be used without any limitation as long as it has a refractive index of 1.52 to 1.58 after polymerization. The refractive index of the polymerizable monomer (A) after polymerization is preferably 1.525 to 1.58, and more preferably 1.53 to 1.58, to make it easier to increase the difference in refractive index from the inorganic particles (B). As stated herein, the refractive index of the polymerizable monomer (A) after polymerization means the refractive index of the polymer of the polymerizable monomer (A). To obtain a desired refractive index of the polymerizable monomer (A) after polymerization, one kind of polymerizable monomer may be selected, or several kinds of polymerizable monomers having different refractive indices may be mixed at an appropriate ratio, with taking into consideration that a polymer obtained by polymerizing a polymerizable monomer generally tends to have a slightly higher refractive index than the polymerizable monomer itself.

Among the above-mentioned polymerizable monomers (A), a radical polymerizable monomer is used suitably. Specific examples of the radical polymerizable monomer in the polymerizable monomer (A) include esters of α-cyanoacrylic acid, (meth)acrylic acid, α-halogenated acrylic acid, crotonic acid, cinnamic acid, sorbic acid, maleic acid, itaconic acid, etc., (meth)acrylamide, (meth)acrylamide derivatives, vinyl esters, vinyl ethers, mono-N-vinyl derivatives, and styrene derivatives. Among them, (meth)acrylic acid esters are preferred. In the present invention, "(meth)acryl" means methacryl or acryl.

Examples of (meth)acrylic acid ester-based polymerizable monomers are given hereinbelow.

(I) Monofunctional (meth)acrylates include: methyl (meth)acrylate, isobutyl (meth)acrylate, benzyl (meth)acrylate, lauryl (meth)acrylate, 2,3-dibromopropyl (meth)acrylate, 2-hydroxyethyl (meth)acrylate, 6-hydroxyhexyl (meth) acrylate, 10-hydroxydecyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N-(dihydroxyethyl) (meth)acrylamide, (meth)acryloyloxydodecylpyridinium bromide, (meth)acryloyloxydodecylpyridinium chloride, (meth)acryloyloxyhexadecylpyridinium chloride, and (meth) acryloyloxydecylammonium chloride.

(II) Bifunctional (meth)acrylates include:
ethylene glycol di(meth)acrylate, triethylene glycol di(meth)acrylate, propylene glycol di(meth)acrylate, neopentyl glycol di(meth)acylate, 1,6-hexanediol di(meth)acrylate, 1,10-decanediol di(meth)acrylate, bisphenol A diglycidyl (meth)acrylate (2,2-bis[4-[3-(meth)acryloyloxy-2-hydroxypropoxy]phenyl]propane, commonly known as "BisGMA"), 2,2-bis[4-(meth)acryloyloxyethoxyphenyl] propane, 2,2-bis[4-(meth)acryloyloxypolyethoxyphenyl] propane, 1,2-bis[3-(meth)acryloyloxy-2-hydroxypropoxy] ethane, pentaerythritol di(meth)acrylate, and [2,2,4-trimethylhexamethylenebis(2-carbamoyloxyethyl)] dimethacrylate (commonly known as "UDMA").

(III) Trifunctional or higher polyfunctional (meth)acrylates include:
trimethylolpropane tri(meth)acrylate, trimethylolethane tri(meth)acrylate, tetramethylolmethane tri(meth)acrylate, pentaerythritol tetra(meth)acrylate, dipentaerythritol hexa (meth)acrylate, N,N'-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane.

To improve the adhesion to tooth structures, metals, ceramics, and the like, it is preferable in some cases that the curable composition of the present invention contain, as a polymerizable monomer, a functional monomer for providing adhesion to these adherends.

As such functional monomers, for example, monomers having a phosphoric acid group, such as 2-(meth)acryloyloxyethyl dihydrogenphosphate, 10-(meth)acryloyloxydecyl dihydrogenphosphate, and 2-(meth)acryloyloxyethyl phenyl hydrogenphosphate, and monomers having a carboxylic acid group, such as 11-(meth)acryloyloxy-1,1-undecanedicarboxylic acid and 4-(meth)acryloyloxyethoxycarbonyl phthalic acid are preferred because these monomers exhibit excellent adhesion to tooth structures and base metals.

As such functional monomers, for example, 10-mercaptodecyl (meth)acrylate, 6-(4-vinylbenzyl-n-propyl)amino-1,3,5-triazine-2,4-dithione, a thiouracil derivative described in JP 10 (1998)-1473 A, and a sulfur element-containing compound described in JP 11(1999)-92461 A are preferred because these monomers exhibit excellent adhesion to precious metals.

Furthermore, as such a functional monomer, for example, a silane coupling agent such as γ-methacryloxypropyltrimethoxysilane is effective in bonding to ceramics, porcelains, and dental composite resins.

The content of the polymerizable monomer (A) is preferably 8 to 40% by weight, and more preferably 15 to 35% by weight, with respect to the total weight of the dental curable composition. When the content of the polymerizable monomer (A) is less than 8%, the resulting paste may be too viscous or too fluid, which may result in poor handling properties of the dental curable composition. When the content of the polymerizable monomer (A) is more than 40% by weight, the inorganic filler is insufficient in amount, which may result in the dental curable composition providing the poor mechanical strength.

Inorganic Particles (B)

As the inorganic particles (B) used in the present invention, any inorganic particles can be used without any limitation as long as they have a refractive index of 1.43 to 1.50 and are aggregates of inorganic fine particles having an average primary particle size of 2 to 50 nm. When the refractive index of the inorganic particles (B) is less than 1.43, the differences in refractive index from the polymer of the polymerizable monomer (A) and from the inorganic particles (C) are too large, which results in poor transparency. When the refractive index of the inorganic particles (B) is more than 1.50, the differences in refractive index from the polymer of the polymerizable monomer (A) and from the inorganic particles (C) are too small, which results in poor light diffusion. The refractive index of the inorganic particles (B) is preferably 1.43 to 1.48, and more preferably 1.43 to 1.46, to make it easier to increase the differences in refractive index from the polymer of the polymerizable monomer (A) and from the inorganic particles (C). Furthermore, it is preferable that the difference between the refractive index of the polymerizable monomer (A) after polymerization and that of the inorganic particles (B), i.e., {(A)-(B)}, be 0.05 or more. In this case, particularly excellent light diffusion is obtained. The average primary particle size of the inorganic particles (B) is preferably 5 to 35 nm, and more preferably 7 to 20 nm, to make it easier to increase the number of interfaces between the inorganic particles (B) and the polymerizable monomer (A), which are the sites for refraction and scattering of light, and to obtain aggregates having adequate strength. The average primary particle size of the inorganic particles (B) can be measured by taking electron micrographs of these inorganic particles (B) and calculating the average value of the diameters of the 100 randomly-selected primary particles. If the primary particles are non-spherical particles, their diameters are obtained by calculating the arithmetic mean of the longest and shortest dimensions thereof.

The average particle size of the inorganic particles (B) is not limited to any particular size as long as the inorganic particles (B) are aggregates having the above-mentioned refractive index and average primary particle size. The average particle size of the inorganic particles (B) is preferably 1.0 to 20 μm, more preferably 2.0 to 15 μm, and particularly preferably 3 to 10 μm, to make it easier to obtain the light diffusion and transparency of the cured product of the composition. When the average particle size is less than 1.0 μm, the function of adjusting transmission of light is reduced. Therefore, an increased amount of the inorganic particles (B) must be added, which may reduce the light diffusion and transparency of the cured product. On the other hand, when the average particle size is more than 20 μm, light is refracted and scattered more strongly, which may reduce the transparency of the cured product. Furthermore, even if the inorganic particles (B) are aggregates having an average primary particle size of 2 to 50 nm, the polishability (particularly ease of polishing) may decrease. The average particle size of the inorganic particles (B) can be obtained by the laser diffraction/scattering method. More specifically, for example, the average particle size can be obtained by the measurement using a 0.2% aqueous solution of sodium hexametaphosphate as a dispersion medium, with a laser diffraction particle size distribution analyzer (SALD-2100, manufactured by Shimadzu Corporation).

The specific surface area and pore volume of the inorganic particles (B) are not limited to any particular ones as long as the inorganic particles (B) are aggregates having the above-mentioned refractive index and average primary particle size. To make it easier to obtain the light diffusion and transparency of the cured product, the specific surface area and the pore volume are preferably 50 to 400 $m^2/g$ and 0.05 to 1.5 mL/g, respectively. More preferably, the specific surface area and the pore volume are 100 to 300 $m^2/g$ and 0.1 to 1.0 mL/g, respectively. Particularly preferably, the specific surface area and the pore volume are 100 to 250 $m^2/g$ and 0.15 to 0.5 mL/g, respectively.

As the material of the inorganic particles (B), any material can be used without any limitation as long as the inorganic particles (B) satisfy the above-mentioned relationship between the refractive index and the average primary particle size. Examples of such materials include: silica prepared by flame pyrolysis (for example, AEROSIL OX 50, AEROSIL Ar 130, AEROSIL Ar 200, etc., manufactured by Japan Aerosil Co., Ltd.); silica sol prepared by the wet method (for example, SNOWTEX series manufactured by Nissan Chemical Industries, Ltd., and CATALOID series manufactured by JGC Catalysts and Chemicals Ltd.); and silica particles prepared by the sol-gel method. Composite materials with ions of other metals also can be used as long as they satisfy the above-mentioned range of refractive indices. The other metals are not particularly limited. Preferable examples of such metals include Al, Ti, Zr, Sr, Ba, La, Na, K, Ca, and Mg, from the viewpoints of ease of adjusting the refractive index and safety. Any of these metals may be added as a soluble metal salt into a silica sol in which silica particles have already been dispersed. Any of these metals also may be added during the synthesis of silica particles to obtain composite oxide particles.

As the method for producing the inorganic particles (B), any of the following common methods can be used without any limitation, but the method is not particularly limited to the followings. The easiest aggregation process is to disperse primary particles in a dispersion medium and then remove the medium by heating or pressure reduction. Another available aggregation process is so-called spray drying, in which a dispersion of primary particles is sprayed in the form of a fine mist into a drying chamber to obtain dried aggregated particles. In the former aggregation method, since larger size aggregates are obtained, additional steps such as crushing and grinding must be performed. The latter spray drying is more efficient because these steps can be omitted. An example of such particles produced by this spray drying is Silica Microbeads manufactured by JGC Catalysts and Chemicals Ltd.

After the aggregation process, the inorganic particles (B) may be subjected to heat treatment, if necessary, to adjust the cohesion of particles or to remove water or organic substances. The temperature of the heat treatment is in the range of 200° C. or higher but 800° C. or lower for many compositions of primary particles, although it cannot be determined definitely because the optimal treatment conditions (such as a temperature and a time duration) vary depending on the composition of primary particles and the material used therefor. When the calcination temperature is lower than 200° C., water and organic substances tend to remain, which makes it difficult to obtain a cured product having sufficient transparency. On the other hand, a calcination temperature of higher than 800° C. is not preferable because the components of the composition often begin to crystallize, fuse, or sinter at that temperature, which may reduce the polishability and transparency of the cured product of the composition containing the inorganic particles (B). More specific calcination conditions are determined by the following steps: preparing fillers by calcination at temperatures in this range under different sets of conditions, and subjecting the fillers to powder X-ray diffraction analysis so as to confirm that no crystal structure is observed therein; and further preparing compositions containing these inorganic particles (B), and measuring the degrees of smoothness and gloss of the polished surfaces of the cured products of the compositions and measuring the degrees of transparency thereof. That is, when the heat treatment of the inorganic particles (B) is insufficient, it is difficult to obtain sufficient transparency. When the heat treatment is excessive, not only the appearance of the cured product becomes unnaturally opaque but also the smoothness and gloss of the polished surface of the cured product decrease significantly. Presumably, these phenomena are attributed to the following reasons. When the inorganic particles (B) are heated at an excessively high temperature, a part of the components begin to crystallize. Along with the crystallization, the refractive index of the inorganic particles (B) increases, and the composition containing the inorganic particles (B) shows unnatural whiteness, which is different from the whiteness of natural teeth. Furthermore, as the hardness of the inorganic particles (B) increases, the cured product is more resistant to abrasion, which decreases the polishability thereof.

The inorganic particles (B) are used in combination with the polymerizable monomer (A) for the dental curable composition. Therefore, it is desirable that the inorganic particles (B) be subjected previously to surface treatment with a surface treating agent to improve the affinity for the polymerizable monomer (A), and to increase the chemical bonding with the polymerizable monomer (A) so as to enhance the mechanical strength of the cured product of the composition. In the case where the inorganic particles (B) are subjected to surface treatment, the refractive index of the inorganic particles (B) refers to the refractive index after the surface treatment.

Examples of such surface treating agents include at least one organic metal compound selected from the group consisting of an organic silicon compound, an organic titanium compound, an organic zirconium compound, and an organic aluminum compound. When two or more different kinds of organic metal compounds are used, the surface-treated layer may be made of a mixture of these two or more different kinds of organic metal compounds, or may have a multilayer structure in which the two or more different organic metal compound layers are laminated.

An example of the organic silicon compound is a compound represented by $R^1{}_n SiX_{4-n}$ (where $R^1$ is a substituted or unsubstituted hydrocarbon group having 1 to 12 carbon atoms, X is an alkoxy group having 1 to 4 carbon atoms, a hydroxyl group, a halogen atom, or a hydrogen atom, and n is an integer of 0 to 3. If a plurality of $R^1$s and a plurality of Xs are present, the $R^1$s may be the same as or different from one another, and the Xs may be the same as or different from one another.)

Specific examples of the organic silicon compound include methyltrimethoxysilane, dimethyldimethoxysilane, phenyltrimethoxysilane, diphenyldimetoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyl-tris(β-methoxyethoxy)silane, 3,3,3-trifluoropropyl trimethoxysilane, methyl-3,3,3-trifluoropropyl dimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropylmethyldiethoxysilane, N-β(aminoethyl)γ-aminopropylmethyldimethoxysilane, N-β(aminoethyl)γ-aminopropyltrimethoxysilane, N-β(aminoethyl)γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyl trimethoxysilane (having 3 to 12 carbon atoms between a (meth)acryloxy group and a silicon atom, for example, γ-methacryloxypropyltrimethoxysilane, or the like), and ω-(meth)acryloxyalkyl triethoxysilane (having 3 to 12 carbon atoms between a (meth)acryloxy group and a silicon atom, for example, γ-methacryloxypropyltriethoxysilane, or the like).

Among them, a coupling agent having a functional group that is copolymerizable with the polymerizable monomer (A), for example, ω-(meth)acryloxyalkyl trimethoxysilane (having 3 to 12 carbon atoms between a (meth)acryloxy group and a silicon atom), ω-(meth)acryloxyalkyl triethoxysilane (having 3 to 12 carbon atoms between a (meth)acryloxy group and a silicon atom), vinyltrimethoxysilane, vinyltriethoxysilane, vinyltriacetoxysilane, γ-glycidoxypropyltrimethoxysilane, or the like is used particularly preferably.

Examples of the organic titanium compound include tetramethyl titanate, tetraisopropyl titanate, tetra-n-butyl titanate, butyl titanate dimmer, and tetra(2-ethylhexyl)titanate.

Examples of the organic zirconium compound include zirconium isopropoxide, zirconium-n-butoxide, zirconium acetylacetonate, and zirconyl acetate.

Examples of the organic aluminum compound include aluminum acetylacetonate and a chelate compound of a salt of aluminum and an organic acid.

When the content of the inorganic particles (B) is 0.1 to 10% by weight with respect to the total weight of the dental curable composition, the resulting cured product exhibits adequate light diffusion and transparency. When the content of the inorganic particles (B) is less than 0.1% by weight, the fraction of the sites for refraction and scattering is too small in the cured product, and the function of diffusing transmitted light is reduced. As a result, sufficient light diffusion is not obtained, although the transparency of the cured product is increased. When the content is more than 10% by weight, light diffusion is obtained, but the fraction of the sites for refraction and scattering is too large in the cured product, and sufficient transparency is not obtained. In order to provide light diffusion and transparency to the cured product in a balanced manner, the content is preferably 0.5 to 8.0% by weight, and more preferably 1.0 to 7.0% by weight.

Inorganic Particles (C)

As the inorganic particles (C) used in the present invention, any inorganic particles can be used without any limitation as long as they have a refractive index of 1.52 to 1.58. When the refractive index of the inorganic particles (C) is less than 1.52, the difference in refractive index from the polymer of the polymerizable monomer (A) tends to be too large and the difference in refractive index from the inorganic particles (B) tends to be too small, which results in poor light diffusion and transparency. When the refractive index of the inorganic particles (C) is more than 1.58, the differences in refractive index from the polymer of the polymerizable monomer (A) and the inorganic particles (B) tend to be too large, which results in a white and opaque cured product with poor transparency. The refractive index of the inorganic particles (C) is preferably 1.525 to 1.58, and more preferably 1.53 to 1.58, to make it easier to decrease the difference in refractive index from the polymer of the polymerizable monomer (A) and to increase the difference in refractive index from the inorganic particles (B). Furthermore, it is preferable that the difference between the refractive index of the polymerizable monomer (A) after polymerization and that of the inorganic particles (B) be 0.03 or less as an absolute value. In this case, particularly excellent transparency is obtained.

Preferably, the inorganic particles (C) contain non-aggregated inorganic particles (C-I) having an average particle size of 0.1 to 1.0 μm, to make it easier to obtain the mechanical strength and polishability of the cured product of the composition as well as the handling properties of the paste. When the average particle size is less than 0.1 μm, satisfactory polishability of the cured product is obtained, but the paste tends to be sticky. In addition, it is difficult to increase the filler content, which may reduce the mechanical strength. When the average particle size is more than 1.0 μm, sufficient mechanical strength is obtained, but the polishability may decrease. The average particle size of the inorganic particles (C-I) is more preferably 0.2 to 0.7 μm, and further preferably 0.2 to 0.4 μm, from the viewpoints of the mechanical strength and polishability of the cured product as well as the handling properties of the paste. The average particle size of the inorganic particles (C-I) can be obtained by the laser diffraction/scattering method. More specifically, for example, the average particle size can be obtained by the measurement using a 0.2% aqueous solution of sodium hexametaphosphate as a dispersion medium, with a laser diffraction particle size distribution analyzer (SALD-2100, manufactured by Shimadzu Corporation).

As the inorganic particles (C-I), any inorganic particles can be used without any limitation as long as they are non-aggregated inorganic particles having a refractive index of 1.52 to 1.58 and an average particle size of 0.1 to 1.0 μm. Examples of the inorganic particles include: various kinds of glass powders [containing silica as a main component and further containing an oxide of a heavy metal, boron, aluminum, and the like, if necessary: e.g., glass powders for dental use, such as E-glass, strontium boroaluminosilicate glass (Ray-Sorb T-3000, manufactured by Kimble, and GM 27884 and 8235, manufactured by Schott), barium silicate glass (Ray-Sorb T-2000, manufactured by Kimble), and lanthanum glass ceramics (GM 31684, manufactured by Schott)]; various kinds of ceramics; composite oxides such as silica-titania, and silica-zirconia; kaolin; clay minerals (such as montmorillonite); mica; ytterbium fluoride; yttrium fluoride; and the like. Any one of the above-mentioned inorganic particles can be used alone or as a mixture of two or more kinds thereof. Among the above inorganic particles, those containing silica as a main component are preferably used as the inorganic particles (C-I) for the dental curable composition of the present invention.

In order to provide good handling properties to the paste in addition to sufficient polishability and mechanical physical properties, it is preferable that the inorganic particles (C) contain inorganic particles (C-II) having an average particle size of 1 to 20 μm in addition to the above-mentioned inorganic particles (C-I). The inorganic particles (C-II) are aggregates containing silica-based fine particles with an average particle size of 2 to 50 nm and an oxide of at least one heavy metal. The average particle size of the silica-based fine particles contained in the inorganic particles (C-II) is preferably 5 to 35 nm, and more preferably 7 to 20 nm, to make it easier to obtain aggregates having adequate strength. The average particle size of the silica-based fine particles contained in the inorganic particles (C-II) can be measured by taking electron micrographs of these silica-based fine particles and calculating the average value of the diameters of the 100 randomly-selected silica-based fine particles. If the silica-based fine particles are non-spherical particles, their diameters are obtained by calculating the arithmetic mean of the longest and shortest dimensions thereof.

The average particle size of the inorganic particles (C-II) is preferably 1.0 to 20 μm, more preferably 2.0 to 15 μm, and particularly preferably 3 to 10 μm. When the average particle size is less than 1.0 μm, the content of the filler having a large specific surface area and a small particle size is high, which may inhibit the effect of enhancing the handling properties. When the average particle size is more than 20 μm, the polishability (particularly ease of polishing) may decrease. The average particle size of the inorganic particles (C-ID can be obtained by the laser diffraction/scattering method. More specifically, for example, the average particle size can be obtained by the measurement using a 0.2% aqueous solution of sodium hexametaphosphate as a dispersion medium, with a laser diffraction particle size distribution analyzer (SALD-2100, manufactured by Shimadzu Corporation).

The weight ratio between the inorganic particles (C-I) and the inorganic particles (C-II) is preferably 1:4 to 4:1, and more preferably 1:3 to 3:1, to make it easier to obtain better paste properties such as spreading and stickiness of the paste and to obtain an easier-to-fill paste.

As the inorganic particles (C-II), any particles can be used without any limitation as long as they are aggregates containing silica-based fine particles with an average particle size of 2 to 50 nm and an oxide of at least one heavy metal, and have a refractive index of 1.52 to 1.58 and an average particle size of 1 to 20 μm. As such particles, aggregates produced by using composite materials between commercially available silica sols (for example, SNOWTEX series manufactured by Nissan Chemical Industries, Ltd., and CATALOID series manufactured by JGC Catalysts and Chemicals Ltd.), silica particles produced by the sol-gel method, or the like and other heavy metal ions can be used. The heavy metals are not particularly limited. Preferable examples of such heavy metals include Al, Ti, Zr, Sr, Ba, La, Y, Yb, etc., from the viewpoints of ease of adjusting the refractive index and safety. Any of these heavy metals may be added as a soluble metal salt into a silica sol in which silica-based particles have already been dispersed. Any of these heavy metals also may be added during the synthesis of silica-based particles to obtain composite oxide particles. Alternatively, aggregates produced from a dispersion of inorganic particles with a chain or network structure in which a plurality of silica-based fine particles are connected through composite oxide coatings containing at least Si, Zr and O may be used. As the aggregation process for the inorganic particles (C-II), the same aggregation process as that for the inorganic particles (B) mentioned above can be employed without any limitation.

The above-mentioned inorganic particles (C) are used in combination with the polymerizable monomer (A) for the dental curable composition. Therefore, it is desirable that the inorganic particles (C) be subjected previously to surface treatment with a surface treating agent to improve the affinity for the polymerizable monomer (A), and to increase the chemical bonding with the polymerizable monomer (A) so as to enhance the mechanical strength of the cured product. As the surface treatment method, the same method as that for the inorganic particles (B) mentioned above can be used without any limitation. In the case where the inorganic particles (C) are subjected to surface treatment, the refractive index of the inorganic particles (C) refers to the refractive index after the surface treatment.

The content of the inorganic particles (C) is preferably 59.9 to 91.9% by weight, and more preferably 64.9 to 84.9% by weight, with respect to the total weight of the dental curable composition. When the content of the inorganic particles (C) is less than 59.9% by weight, the inorganic filler is insufficient in amount, which may result in the dental curable composition providing the poor mechanical strength. When the content of the inorganic particles (C) is more than 91.9% by weight, the resulting paste may be too viscous or too fluid, which may result in poor handling properties of the dental curable composition.

Inorganic Ultrafine Particles (D)

The dental curable composition of the present invention may contain inorganic ultrafine particles (D) in addition to the inorganic particles (B) and the inorganic particles (C), to enhance the handling properties thereof as a paste. As the inorganic ultrafine particles (D), any known inorganic ultrafine particles used in dental curable compositions are used without any limitation. Preferable examples of the inorganic ultrafine particles (D) include particles of inorganic oxides such as silica, alumina, titania, and zirconia, particles of composite oxides of any of these oxides, and particles of calcium phosphate, hydroxyapatite, yttrium fluoride, and ytterbium fluoride. Preferably, the inorganic ultrafine particles (D) are particles of silica, alumina, titania, or the like prepared by flame pyrolysis, and examples thereof include products manufactured by Japan Aerosil Co., Ltd. under the trade names of Aerosil, Aeroxide Alu C, Aeroxide $TiO_2$ P 25, Aeroxide $TiO_2$ P 25S, VP Zirconium Oxide 3-YSZ, and VP Zirconium Oxide 3-YSZ PH.

The average particle size of the inorganic ultrafine particles (D) is preferably 5 to 50 nm, and more preferably 10 to 40 nm. The average particle size of the inorganic ultrafine particles (D) can be measured by taking electron micrographs of these ultrafine particles (D) and calculating the average value of the diameters of the 100 randomly-selected ultrafine particles. If the ultrafine particles are non-spherical particles, their diameters are obtained by calculating the arithmetic mean of the longest and shortest dimensions thereof.

Like the inorganic particles (C), the inorganic ultrafine particles (D) are used in combination with the polymerizable monomer (A) for the dental curable composition. Therefore, it is desirable that the inorganic ultrafine particles (D) be subjected previously to surface treatment with a surface treating agent to improve the affinity for the polymerizable monomer (A), and to increase the chemical bonding with the polymerizable monomer (A) so as to enhance the mechanical strength of the cured product. As the surface treatment method, the same method as that for the inorganic particles (B) mentioned above can be used without any limitation.

The content of the inorganic ultrafine particles (D) is preferably 1 to 10% by weight and more preferably 1 to 5% by weight, with respect to the total weight of the dental curable composition.

It is preferable that the dental curable composition of the present invention further contain a polymerization initiator to facilitate polymerization and curing. The polymerization initiator can be selected from polymerization initiators commonly used in the industrial field. Among them, polymerization initiators used for dental applications are used preferably. Particularly, photopolymerization initiators and chemical polymerization initiators are used alone, or two or more of them are used in suitable combination.

Examples of the photopolymerization initiator include (bis)acylphosphine oxides, water-soluble acylphosphine oxides, thioxanthones or quaternary ammonium salts of thioxanthones, ketals, α-diketones, benzoin alkyl ether compounds, and α-amino ketone compounds.

Among (bis)acylphosphine oxides used as the photopolymerization initiator, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

Preferably, the water-soluble acylphosphine oxides used as the photopolymerization initiator have alkali metal ions, alkaline earth metal ions, pyridinium ions, or ammonium ions in the acylphosphine oxide molecules. For instance, the water-soluble acylphosphine oxides can be synthesized by the method disclosed in EP 0009348 B1 or JP 57 (1982)-197289 A.

Specific examples of the aforementioned water-soluble acylphosphine oxides include sodium monomethylacetylphosphonate, sodium monomethyl(1-oxopropyl)phosphonate, sodium monomethylbenzoylphosphonate, sodium monomethyl(1-oxobutyl)phosphonate, sodium monomethyl(2-methyl-1-oxopropyl)phosphonate, sodium acetylphosphonate, sodium monomethylacetylphosphonate, sodium acetylmethylphosphonate, methyl-4-(hydroxymethoxyphosphinyl)-4-oxobutanoate sodium salt, methyl-4-oxophosphonobutanoate monosodium salt, acetylphenylphosphinate sodium salt, sodium (1-oxopropyl) pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-diethoxyethyl)methylphosphinate, sodium (1,1-diethoxyethyl)methylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl)phosphinate sodium salt, methyl(2-methyl-1,3-thiazolidin-2-yl)phosphonite sodium salt, (2-methylperhydro-1,3-diazin-2-yl)phosphonite sodium salt, acetylphosphinate sodium salt, (1,1-diethoxyethyl)phosphonite sodium salt, (1,1-diethoxyethyl)methylphosphonite sodium salt, methyl(2-methyloxathiolane-2-yl)phosphinate sodium salt, methyl(2,4,5-trimethyl-1,3-dioxolan-2-yl)phosphinate sodium salt, methyl(1,1-propoxyethyl)phosphinate sodium salt, (1-methoxyvinyl)methylphosphinate sodium salt, (1-ethylthiovinyl)methylphosphinate sodium salt, methyl(2-methylperhydro-1,3-diazin-2-yl)phosphinate sodium salt, methyl(2-methylperhydro-1,3-thiazin-2-yl)phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyl)phosphinate sodium salt, acetylmethylphosphinate oxime sodium salt, acetylmethylphosphinate-O-benzyloxime sodium salt, 1-[(N-ethoxyimino)ethyl]methylphosphinate sodium salt, methyl(1-phenyliminoethyl)phosphinate sodium salt, methyl(1-phenylhydrazone ethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethyl)methylphosphinate sodium salt, (dimethoxymethyl)methyl phosphinate sodium salt, formylmethylphosphinate sodium salt, (1,1-dimethoxypropyl)methylphosphinate sodium salt, methyl(1-oxopropyl)phosphinate sodium salt, dodecylguanidine salt of (1,1-dimethoxypropyl)methylphosphinate, isopropylamine salt of (1,1-dimethoxypropyl)methylphosphinate, acetylmethylphosphinate thiosemicarbazone sodium salt, 1,3,5-tributyl-4-methylamino-1,2,4-triazolium (1,1-dimethoxyethyl)-methylphosphinate, 1-butyl-4-butylaminomethylamino-3,5-dipropyl-1,2,4-triazolium (1,1-dimethoxyethyl)-methylphosphinate, 2,4,6-trimethylbenzoylphenylphosphine oxide sodium salt, 2,4,6-trimethylbenzoylphenylphosphine oxide potassium salt, and ammonium salt of 2,4,6-trimethylbenzoylphenylphosphine oxide. Furthermore, examples thereof also include compounds described in JP 2000-159621A.

Among these (bis)acylphosphine oxides and water-soluble acylphosphine oxides, particularly preferable ones are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt.

Examples of thioxanthones or the quaternary ammonium salts of thioxanthones that are used as the aforementioned photopolymerization initiators include thioxanthone, 2-chlorothioxanthen-9-one, 2-hydroxy-3-(9-oxy-9H-thioxanthen-4-yloxy)-N,N,N-trimethyl-propaneaminium chloride, 2-hydroxy-3-(1-methyl-9-oxy-9H-thioxanthen-4-yloxy)-N,N,N-trimethyl-propaneaminium chloride, 2-hydroxy-3-(9-oxo-9H-thioxanthen-2-yloxy)-N,N,N-trimethyl-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Among the thioxanthones or the quaternary ammonium salts of thioxanthones, a particularly preferable thioxanthone is 2-chlorothioxanthen-9-one, and a particularly preferable quaternary ammonium salt of thioxanthone is 2-hydroxy-3-(3,4-dimethyl-9H-thioxanthen-2-yloxy)-N,N,N-trimethyl-1-propaneaminium chloride.

Examples of the ketals used as the aforementioned photopolymerization initiator include benzyl dimethyl ketal and benzyl diethyl ketal.

Examples of the α-diketones used as the aforementioned photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferable from the viewpoint of having the maximum absorption wavelength in the visible light range.

Examples of the benzoin alkyl ethers used as the aforementioned photopolymerization initiator include benzoin methyl ether, benzoin ethyl ether, benzoin isopropyl ether, and benzoin isobutyl ether.

Examples of the α-aminoketones used as the aforementioned photopolymerization initiator include 2-methyl-1-[4-(methylthio)phenyl]-2-morpholinopropan-1-one.

Preferably, among these photopolymerization initiators, at least one selected from the group consisting of (bis)acylphosphine oxides, salts thereof, and α-diketones is used. This makes it possible to obtain a composition that has excellent photo polymerization ability in visible and near-ultraviolet ranges and sufficiently high photo polymerization ability regardless of which light source among a halogen lamp, light-emitting diode (LED), and xenon lamp is used.

Among the polymerization initiators used in the present invention, a chemical polymerization initiator that is used preferably is organic peroxide. The organic peroxide used as the aforementioned chemical polymerization initiator is not particularly limited and a known one can be used. Examples of typical organic peroxides include ketone peroxide, hydroperoxide, diacyl peroxide, dialkyl peroxide, peroxyketal, peroxyester, and peroxydicarbonate.

Examples of the ketone peroxide used as the aforementioned chemical polymerization initiator include methyl ethyl ketone peroxide, methyl isobutyl ketone peroxide, methylcyclohexanone peroxide, and cyclohexanone peroxide.

Examples of the hydroperoxide used as the aforementioned chemical polymerization initiator include 2,5-dimethylhexane-2,5-dihydroperoxide, diisopropylbenzene hydroperoxide, cumene hydroperoxide, and t-butyl hydroperoxide.

Examples of the diacyl peroxide used as the aforementioned chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxide used as the aforementioned chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketal used as the aforementioned chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester.

Examples of the peroxyester used as the aforementioned chemical polymerization initiator include α-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethyl hexanoate, t-butylperoxy acetate, t-butylperoxy benzoate, and t-butylperoxymaleic acid.

Examples of the peroxydicarbonate used as the aforementioned chemical polymerization initiator include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, diacyl peroxides are used preferably from the viewpoint of a comprehensive balance of safety, storage stability, and radical production ability, and among these, benzoyl peroxide is used particularly preferably.

The content of the polymerization initiator used in the present invention is not particularly limited. However, from the viewpoint of, for example, curability of the resultant composition, it is preferable that 0.01 to 10 parts by weight of the polymerization initiator be contained per 100 parts by weight of the polymerizable monomer (A), and it is more preferable that 0.1 to 5 parts by weight of the polymerization initiator be contained. When the content of the polymerization initiator is less than 0.01 part by weight, polymerization may not proceed sufficiently and thereby mechanical strength may be reduced. Therefore, the content is more preferably at least 0.1 part by weight. On the other hand, when the content of the polymerization initiator exceeds 10 parts by weight, in the case where the polymerization initiator itself has low polymerization performance, sufficient mechanical strength may not be obtained and furthermore precipitation from the composition may occur. Therefore, the content is more preferably 5 parts by weight or less.

In a preferred embodiment, a polymerization accelerator is used. Examples of the polymerization accelerator used in the present invention include amines, sulfinic acids and salts thereof, aldehydes, and thiol compounds.

Amines used as the polymerization accelerator can be classified into aliphatic amines and aromatic amines. Examples of aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferable from the viewpoint of curability and storage stability of the composition, and particularly, N-methyldiethanolamine and triethanolamine are used more preferably.

Examples of aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-(methacryloyloxy)ethyl ester, 4-N,N-dimethylaminobenzophenone, and butyl 4-dimethylaminobenzoate. Among these, at least one selected from the group consisting of N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone is used preferably from the viewpoint of being capable of providing the composition with excellent curability.

Examples of the sulfinic acid or salt thereof used as the polymerization accelerator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Sodium benzenesulfinate, sodium p-toluenesulfinate, and sodium 2,4,6-triisopropylbenzenesulfinate are particularly preferable.

Examples of aldehydes used as the polymerization accelerator include derivatives of terephthalaldehyde and benzaldehyde. Examples of the benzaldehyde derivative include dimethylaminobenzaldehyde, p-methyloxybenzaldehyde, p-ethyloxybenzaldehyde, and p-n-octyloxybenzaldehyde. Among these, from the viewpoint of curability, p-n-octyloxybenzaldehyde is used preferably.

Examples of the thiol compound used as the polymerization accelerator include 3-mercaptopropyltrimethoxysilane, 2-mercaptobenzoxazole, decanethiol, and thiobenzoic acid.

The content of the polymerization accelerator used in the present invention is not particularly limited. However, from the viewpoint of, for example, curability of the resultant composition, it is preferable that 0.001 to 10 parts by weight of polymerization accelerator be contained per 100 parts by weight of the polymerizable monomer component (A), and it is more preferable that 0.001 to 5 parts by weight of the polymerization accelerator be contained. When the content of the polymerization accelerator is less than 0.001 part by weight, polymerization may not proceed sufficiently and mechanical strength may be reduced. Therefore, the content is more preferably at least 0.05 part by weight. On the other hand, when the content of the polymerization accelerator exceeds 10 parts by weight, in the case where the polymerization initiator itself has low polymerization performance, sufficiently high mechanical strength may not be obtained. Therefore, the content is more preferably 5 parts by weight or less.

To the dental curable composition of the present invention, a pH adjuster, an ultraviolet absorber, an antioxidant, a polymerization inhibitor, a colorant, an antibacterial agent, an X-ray contrast agent, a thickening agent, a fluorescent agent, or the like can further be added in accordance with the intended use.

For example, when the cured surface is expected to have a fluorine ion sustained-release property, a fluorine ion sustained-releasable filler, such as fluoroaluminosilicate glass, calcium fluoride, sodium fluoride, or sodium monofluorophosphate also can be added.

When it is expected to have an antibacterial property, for example, a surfactant having an antibacterial activity, such as cetylpyridinium chloride or 12-(meth)acryloyloxydodecylpyridinium bromide, or a photocatalytic titanium oxide can be added.

According to the dental curable composition of the present invention containing the polymerizable monomer (A) showing a refractive index in a specific range after polymerization, the inorganic particles (B) having an average primary particle size in a specific range and a refractive index in a specific range, and the inorganic particles (C) having a refractive index in a specific range different from that of the inorganic particles (B), the resulting cured product exhibits excellent light diffusion and transparency in a balanced manner. The use of these two types of inorganic particles makes it possible to obtain higher mechanical strength without impairing the surface smoothness and gloss after polishing and the retention of the smoothness and gloss. In addition, the cured product has high surface smoothness and gloss after polishing and retention of the smoothness and gloss, and therefore, the dental material using the dental curable composition of the present invention offers a good aesthetic appearance. Furthermore, the dental curable composition of the present invention has good handling properties as well as proper fluidity and forming property as a paste, and the adhesion to dental instruments and stickiness are reduced. That is, the dental curable composition is very easy to handle.

The dental curable composition of the present invention can be used suitably in a conventional manner as dental materials, for example, dental composite resins such as dental composite filling materials, dental crown materials, and luting materials, dental adhesives such as orthodontic adhesives, cavity coating adhesives, and dental fissure sealing materials, denture base materials, tissue conditioning materials for denture bases, fissure sealants, coating materials to be applied to tooth surfaces and dental prostheses, surface glazing materials, and dental lacquers. The cured product obtained by polymerizing and curing the dental curable composition of the present invention also can be molded to be used as artificial teeth, dentures, and resin blocks for CAD/CAM. Among them, the dental curable composition of the present invention can be used advantageously as a dental composite resin. This composite resin exhibits both high light diffusion and high transparency and matches natural teeth very well, and has high mechanical strength, and high surface smoothness and gloss after polishing as a cured product as well as excellent handling properties as a paste.

EXAMPLES

The present invention will be described in detail below by the following examples and comparative examples, without intending to limit the scope of the present invention to these examples. The test methods, materials, etc. used in the examples are collectively shown below.

[Measurement of Particle Size of Powder]

A laser diffraction particle size distribution analyzer (SALD-2100, manufactured by Shimadzu Corporation) was used to measure the particle size of each of the produced powders. As a dispersion medium, a 0.2% aqueous solution of sodium hexametaphosphate was used. The particle size of a silica sol and that of inorganic ultrafine particles were obtained by taking electron micrographs of these particles.

[Measurement of Pore Volume and Specific Surface Area]

The pore volume and specific surface area were measured with BELSORP-mini II (BEL Japan, Inc.) by the $N_2$ gas adsorption method. The specific surface area was calculated by the BET method.

[Handling Properties]

The dental curable composition thus produced was filled in a cavity of 4 mmφ×4 mm, and the paste properties thereof were evaluated, in terms of ease of filling, according to the following evaluation criteria.

5: Particularly excellent in forming property. Paste spreads very well. Not sticky and remarkably easy to fill.

4: Excellent in forming property. Paste spreads very well. Not sticky and very easy to fill.

3: Having forming property. Paste spreads well. Not sticky and easy to fill.

2: Either forming property or spreading of paste is poor, or the paste is sticky and difficult to fill.

1: Forming property, spreading, and stickiness of paste are all poor and unsuitable for practical use. Impractical to fill.

The pastes rated 3, 4 and 5 are suitable for practical use.

[Stability of Paste Properties]

The pasty dental curable composition thus produced was filled in a syringe for CLEARFIL MAJESTY (manufactured by Kuraray Medical Inc.), and allowed to stand still for 1 hour in a thermostatic chamber at 25° C. (with a humidity of 40%). After the standing, the paste was placed in a mound at the center of a glass plate (5 cm×5 cm), another glass plate (5 cm×5 cm) was placed on the mound of paste, and 1.0 kg of weight was applied thereon. After 30 seconds, the longest and shortest diameters of the paste were measured through the glass plate, and the arithmetic mean of these diameters was calculated to obtain the consistency. The pasty dental curable composition thus produced also was filled in a syringe for CLEARFIL MAJESTY (manufactured by Kuraray Medical Inc.), placed in a thermostatic chamber at 50° C. (with a humidity of 40%) for one week, and then allowed to stand still for 1 hour in a thermostatic chamber at 25° C. (with a humidity of 40%). Then, the consistency was measured in the same manner as described above. The difference (amount of change) between the consistency after 1-hour standing at 25° C. and the consistency after 1-week standing at 50° C. was calculated. The paste that showed the amount of change within ±1.5 mm was regarded as an acceptable one.

[Flexural Strength of Cured Product]

A test sample (2 mm×2 mm×30 mm) of the cured product of the produced dental curable composition was prepared. The test sample was immersed in water at 37° C. for 24 hours. Then, the flexural strength of the test sample was measured using a universal testing machine (manufactured by Instron) with a span being set at 20 mm and a crosshead speed being set at 1 mm/min according to a three-point flexural test method.

[Polishability]

The produced dental curable composition was filled in a stainless steel mold (with a thickness of 1 mm and a diameter of 15 mm). The mold was clamped between upper and lower glass slides and the upper and lower surfaces of the mold were each exposed to light irradiation for 2 minutes with a visible light irradiator for dental use (α-Light II, manufactured by Morita Corporation). Thus, the dental curable composition was cured. The cured product was taken out of the mold, and then one surface of the cured product was polished with a #800 waterproof abrasive paper. Then, this polished surface was buffed with a dental polishing kit (EWL 80, manufactured by KAVO) at 3000 rpm for 20 seconds. As a polishing material, Porceny Hydron (manufactured by Tokyo Shizaisha) was used. The gloss of the polished surface was measured with a glossmeter (VG-2000, manufactured by Nippon Denshoku Industries Co., Ltd.) and indicated as a ratio to the specular gloss of 100%. The measurement was performed at an angle of 60 degrees. The appropriate degree of gloss is 75% or more.

[Refractive Index]

The refractive index of each of the produced powders was measured with an Abbe's refractometer by the immersion method, in which a sodium D-line was used as a light source, and diiodomethane in which sulfur is dissolved, 1-bromonaphthalene, methyl salicylate, dimethylformamide, 1-pentanol, or the like was used as a liquid. To measure the refractive index of each of the polymers of the polymerizable monomers (A) used in Examples and Comparative Examples, a test sample prepared in the following manner was used. 0.5 part by weight of α-camphorquinone as a polymerization initiator and 1.0 part by weight of ethyl N,N-dimethylaminobenzoate as a polymerization accelerator were dissolved in 100 parts by weight of the polymerizable monomer (A), and the resulting mixture was degassed and then photopolymerized to obtain a cured product. Then, the cured product was formed into a rectangular parallelepiped of 5 mm×10 mm×20 mm as a test sample.

[Transparency of Cured Product]

A disk-shaped test sample (20 minφ×1.0 mm) of the cured product of the dental curable composition was prepared. The lightness (Lw) of the test sample on a standard white plate placed behind the sample and the lightness (Lb) of the same test sample on a standard black plate placed behind the sample were measured using a spectrophotometer (CM-3610d, manufactured by Minolta Co., Ltd.) equipped with an illuminant C light source with a 2° observer, and the difference between the lightness (Lw) and the lightness (Lb) (ΔL=Lw−Lb) was calculated to be used as a measure of the degree of transparency. A higher value of ΔL means a higher level of the transparency of the cured product. The appropriate degree of transparency is 25 or more.

[Measurement of Total Light Transmittance and Haze]

The produced dental curable composition was filled in a Teflon (registered trademark) mold (with a diameter of 30 mm×a thickness of 0.25 mm). The mold was clamped between upper and lower glass slides, and the upper and lower surfaces of the mold were each exposed to light irradiation for 1 minute. Thus, the dental curable composition was cured. The cured product was taken out of the mold, and then the total light transmittance and haze were measured with a haze meter (NDH-5000, manufactured by Nippon Denshoku Industries Co., Ltd.). The haze was calculated by the following formula (2). Higher values of the total light transmittance and the haze mean a higher level of light diffusion of a cured product. The appropriate total light transmittance is 80% or higher, and the appropriate haze is 70% or higher.

Haze=Diffuse transmittance/Total light transmittance×100(%)     (2)

Preparation Example 1

Preparation of Polymerizable Monomer A-1

0.5 parts by weight of α-camphorquinone as a polymerization initiator and 1.0 part by weight of ethyl N,N-dimethylaminobenzoate as a polymerization accelerator were dissolved in 65 parts by weight of bisphenol A diglycidyl methacrylate (Bis-GMA) and 35 parts by weight of triethylene glycol dimethacrylate to prepare a polymerizable monomer A-1. The refractive index of the polymerizable monomer A-1 after polymerization was 1.55.

Preparation Example 2

Preparation of Polymerizable Monomer A-2

A polymerizable monomer A-2 was prepared in the same manner as in Preparation Example 1 except that 75 parts by weight of Bis-GMA and 25 parts by weight of triethylene glycol dimethacrylate were used. The refractive index of the polymerizable monomer A-2 after polymerization was 1.56.

Preparation Example 3

Preparation of Polymerizable Monomer A-3

A polymerizable monomer A-3 was prepared in the same manner as in Preparation Example 1 except that 25 parts by weight of Bis-GMA, 40 parts by weight of [2,2,4-trimethyl-hexamethylenebis(2-carbamoyloxyethyl)]dimethacrylate (UDMA), and 35 parts by weight of triethylene glycol dimethacrylate were used. The refractive index of the polymerizable monomer A-3 after polymerization was 1.52.

Preparation Example 4

Preparation of Polymerizable Monomer A-4

A polymerizable monomer A-4 was prepared in the same manner as in Preparation Example 1 except that 30 parts by weight of Bis-GMA, 40 parts by weight of UDMA, and 30 parts by weight of triethylene glycol dimethacrylate were used. The refractive index of the polymerizable monomer A-4 after polymerization was 1.53.

Preparation Example 5

Preparation of Polymerizable Monomer A-5

A polymerizable monomer A-5 was prepared in the same manner as in Preparation Example 1 except that 80 parts by weight of neopentyl glycol dimethacrylate and 20 parts by weight of UDMA were used. The refractive index of the polymerizable monomer A-5 after polymerization was 1.50.

Preparation Example 6

Preparation of Inorganic Particles B-1

1000 g of silica sol with an average particle size of 10 to 20 nm (SNOWTEX ST-20, manufactured by Nissan Chemical Industries, Ltd.) was put into an enamel tray, and then dried in a hot air dryer at 90° C. until a constant weight was obtained. The substance thus obtained was calcined in an electric furnace at 400° C. for 1 hour to obtain 200 g of calcined solid material. The calcined solid material thus obtained was ground in a vibratory ball mill for 90 minutes to obtain a powder. 100 parts by weight of the powder thus obtained was subjected to surface treatment with 20 parts by weight of γ-methacryloxypropyltrimethoxysilane (KBM 503, manufactured by Shin-Etsu Chemical Co., Ltd.). As a result, inorganic particles B-1 having an average particle size of 5.6 μm, a refractive index of 1.45, a specific surface area of 154 m$^2$/g, and a pore volume of 0.27 mL/g were obtained.

Preparation Example 7

Preparation of Inorganic Particles B-2

Inorganic particles B-2 having an average particle size of 3.1 μm, a refractive index of 1.45, a specific surface area of 98 m$^2$/g, and a pore volume of 0.13 mL/g were obtained in the same manner as in Preparation Example 6, except that a silica sol with an average particle size of 40 to 50 nm (SNOWTEX ST-OL, manufactured by Nissan Chemical Industries, Ltd.) was used and a calcined solid material was ground in a vibratory ball mill for 180 minutes.

Preparation Example 8

Preparation of Inorganic Particles B-3

Inorganic particles B-3 having an average particle size of 14.8 μm, a refractive index of 1.45, a specific surface area of 290 m$^2$/g, and a pore volume of 0.9 mL/g were obtained in the same manner as in Preparation Example 6, except that a silica sol with an average particle size of 4 to 6 nm (SNOWTEX ST-XS, manufactured by Nissan Chemical Industries, Ltd.) was used and a calcined solid material was ground in a vibratory ball mill for 60 minutes.

Preparation Example 9

Preparation of Inorganic Particles B-4

A pH-adjusted silica sol (with a pH of 2.5) prepared by adding dilute nitric acid to 225 g of a silica sol (SNOWTEX ST-20, manufactured by Nissan Chemical Industries, Ltd.) was added slowly dropwise to 30 g of zirconium acetate (zirconium acetate containing 15 to 16% Zr, manufactured by Sigma-Aldrich Corporation) to obtain a mixed sol. The sol thus obtained was put into an enamel tray, and then dried in a hot air dryer at 90° C. A solid material obtained by drying the sol was subjected to heat treatment in an electric furnace at 550° C. for 1 hour, and then the resulting solid material was ground in a vibratory ball mill for 90 minutes. Thus, a powder having a refractive index of 1.48, an average particle size of 6.4 μm, a specific surface area of 175 m$^2$/g, and a pore volume of 0.2 mL/g was obtained. 100 parts by weight of the powder thus obtained was subjected to surface treatment with 20 parts by weight of γ-methacryloxypropyltrimethoxysilane. As a result, an inorganic particles B-4 were obtained.

Preparation Example 10

Preparation of Inorganic Particles B-5

100 parts by weight of fused quartz having an average particle size of 1.7 μm was subjected to surface treatment with 2 parts by weight of γ-methacryloyloxypropyltrimethoxysilane. As a result, inorganic particles B-5 having a refractive index of 1.46 were obtained.

Preparation Example 11

Preparation of Inorganic Particles B-6

A silica sol having an average particle size of 10 to 20 nm (SNOWTEX ST-20, manufactured by Nissan Chemical Industries, Ltd.) was pre-dried by spray drying with a micro-mist dryer "MDL-050" (manufactured by Fujisaki Electric Co., Ltd.) under the conditions of an inlet temperature of 200°

C., an internal temperature of 80° C., an air flow rate of 30 mL/min, and a liquid flow rate of 15 mL/min. The spherical powder thus obtained was calcined in an electric furnace at 400° C. for 1 hour to obtain a calcined powder. 100 parts by weight of the powder thus obtained was subjected to surface treatment with 20 parts by weight of γ-methacryloxypropyltrimethoxysilane (KBM 503, manufactured by Shin-Etsu Chemical Co., Ltd.). As a result, inorganic particles B-6 having an average particle size of 4.9 μm, a refractive index of 1.45, a specific surface area of 110 m$^2$/g, and a pore volume of 0.17 mL/g were obtained.

Preparation Example 12

Preparation of Inorganic Particles B-7

Inorganic particles B-7 having an average particle size of 1.5 μm, a refractive index of 1.45, a specific surface area of 106 m$^2$/g, and a pore volume of 0.16 mL/g were obtained in the same manner as in Preparation Example 11, except that a silica sol having an average particle size of 10 to 20 nm (SNOWTEX ST-20, manufactured by Nissan Chemical Industries, Ltd.) was diluted with distilled water to 5% by weight, and then was pre-dried under the conditions of an inlet temperature of 200° C., an internal temperature of 80° C., an air flow rate of 55 mL/min, and a liquid flow rate of 15 mL/min.

Preparation Example 13

Inorganic Particles C-1

100 parts by weight of barium glass (8235UF 0.4, having an average particle size of 0.4 μm, manufactured by Schott) was subjected to surface treatment with 8 parts by weight of γ-methacryloxypropyltrimethoxysilane. As a result, inorganic particles C-1 were obtained. The refractive index of the inorganic particles C-1 was 1.55.

Preparation Example 14

Inorganic Particles C-2

100 parts by weight of barium glass (8235UF 0.7, having an average particle size of 0.7 μM, manufactured by Schott) was subjected to surface treatment with 4 parts by weight of γ-methacryloxypropyltrimethoxysilane. As a result, inorganic particles C-2 were obtained. The refractive index of the inorganic particles C-2 was 1.55.

Preparation Example 15

Inorganic Particles C-3

100 parts by weight of barium glass (GM27884 NanoFine 180, having an average particle size of 0.2 μm, manufactured by Schott) was subjected to surface treatment with 13 parts by weight of γ-methacryloxypropyltrimethoxysilane. As a result, inorganic particles C-3 were obtained. The refractive index of the inorganic particles C-3 was 1.53.

Preparation Example 16

Inorganic Particles C-4

Lanthanum glass ceramics (GM31684, manufactured by Shutt) were ground in a vibratory ball mill for 12 hours to obtain a powder. 100 parts by weight of the powder thus obtained was subjected to surface treatment with 4 parts by weight of γ-methacryloxypropyltrimethoxysilane. As a result, inorganic particles C-4 having an average particle size of 0.8 μm were obtained. The refractive index of the inorganic particles C-4 was 1.58.

Preparation Example 17

Inorganic Particles C-5

Inorganic particles C-5 having a refractive index of 1.53, an average particle size of 6.2 μm, a specific surface area of 165 m$^2$/g, and a pore volume of 0.22 mL/g were obtained in the same manner as in Preparation Example 9, except that 55 g of zirconium acetate (zirconium acetate containing 15 to 16% Zr, manufactured by Sigma-Aldrich Corporation) and 225 g of silica sol (SNOWTEX ST-20, manufactured by Nissan Chemical Industries, Ltd.) were used.

Preparation Example 18

Inorganic Particles C-6

Inorganic particles C-6 having a refractive index of 1.55, an average particle size of 6.3 μm, a specific surface area of 160 m$^2$/g, and a pore volume of 0.21 mL/g were obtained in the same manner as in Preparation Example 9, except that 85 g of zirconium acetate (zirconium acetate containing 15 to 16% Zr, manufactured by Sigma-Aldrich Corporation) and 225 g of silica sol (SNOWTEX ST-20, manufactured by Nissan Chemical Industries, Ltd.) were used.

Preparation Example 19

Preparation of Inorganic Ultrafine Particles D-1

100 parts by weight of nearly spherical ultrafine particles having an average particle size of 20 nm (Aerosil 130, manufactured by Nippon Aerosil Corporation) were subjected to surface treatment with 40 parts by weight of γ-methacryloxypropyltrimethoxysilane. As a result, inorganic ultrafine particles D-1 were obtained.

Preparation Example 20

Preparation of Inorganic Ultrafine Particles D-2

100 parts by weight of nearly spherical ultrafine particles having an average particle size of 40 nm (Aerosil OX 50, manufactured by Nippon Aerosil Corporation) were subjected to surface treatment with 7 parts by weight of γ-methacryloxypropyltrimethoxysilane. As a result, inorganic ultrafine particles D-2 were obtained.

Preparation Example 21

Preparation of Inorganic Ultrafine Particles D-3

100 parts by weight of nearly spherical ultrafine particles having an average particle size of 20 nm (Aeroxide AluC, manufactured by Nippon Aerosil Corporation) were subjected to surface treatment with 20 parts by weight of γ-methacryloyloxypropyltrimethoxysilane. As a result, inorganic ultrafine particles D-3 were obtained.

Preparation Example 22

Preparation of Aggregated Particles I described in JP 09 (1997)-255516 A 5 parts by weight of barium glass (8235 having an average particle size of 0.7 μm and a refractive index of 1.55, manufactured by Schott) was dispersed in 95 parts by weight of distilled water, and the resulting dispersion was spray-dried with a spray dryer (L8 type, manufactured by Ohkawara Kakohki Co., Ltd.) to obtain an aggregated powder of barium glass. This dried aggregated powder was placed in an electric furnace and calcined at 700° C. for 3 hours to obtain calcined aggregated particles having an average particle size of 10 μm. The calcined powder was cooled to room temperature in the electric furnace, and then 100 parts by weight of the powder was subjected to surface treatment with 5 parts by weight of γ-methacryloxypropyltrimethoxysilane. As a result, aggregated particles I were obtained as particles for comparison with the inorganic particles (C).

Preparation Example 23

Preparation of Aggregated Particles II Described in JP 09 (1997)-255516 A 100 parts by weight of spherical silica powder having an average particle size of 0.2 μm (SEAHOSTAR having a refractive index of 1.46, manufactured by Nippon Shokubai Co., Ltd.) was aggregated in the presence of 2 parts by weight of polyvinyl alcohol (PVA-117, manufactured by Kuraray Co., Ltd.) by spray drying with a spray dryer (L8 type, manufactured by Ohkawara Kakohki Co., Ltd.). As a result, an aggregated powder composed of nearly spherical particles having an average particle size of about 19 μm was obtained. This aggregated powder was calcined at 950° C. for 1 hour, and then 100 parts by weight of the powder was subjected to surface treatment with 2 parts by weight of γ-methacryloxypropyltrimethoxysilane. As a result, aggregated particles II as particles for comparison with the inorganic particles (B) were obtained.

Examples 1 to 32 and Comparative Examples 1 to 7

The polymerizable monomer, the inorganic particles, and the inorganic ultrafine particles, if necessary, prepared in the manners described above were mixed and kneaded homogeneously in the amounts indicated in Tables 1 to 4, and vacuum-degassed. As a result, the dental curable compositions of Examples 1 to 32 and of Comparative Examples 1 to 7 were obtained. The properties of these dental curable compositions were evaluated in the manners described above. Tables 1 to 6 show the results.

TABLE 1

|  |  |  |  | Examples | | | | | | |
|---|---|---|---|---|---|---|---|---|---|---|
|  |  |  |  | 1 | 2 | 3 | 4 | 5 | 6 | 7 |
| Components of dental curable composition | Polymerizable monomer (A) (weight %) |  | A-1 | 30 | 30 | 30 | 30 | 35 | 35 |  |
|  |  |  | A-2 |  |  |  |  |  |  | 35 |
|  |  |  | A-3 |  |  |  |  |  |  |  |
|  |  |  | A-4 |  |  |  |  |  |  |  |
|  | Inorganic particles (B) (weight %) |  | B-1 | 5 | 0.5 | 2 | 7 | 5 | 5 | 5 |
|  |  |  | B-2 |  |  |  |  |  |  |  |
|  |  |  | B-3 |  |  |  |  |  |  |  |
|  |  |  | B-4 |  |  |  |  |  |  |  |
|  | Inorganic particles (C) (weight %) | (C-I) | C-1 | 65 | 69.5 | 68 | 63 |  |  |  |
|  |  |  | C-2 |  |  |  |  | 60 |  |  |
|  |  |  | C-3 |  |  |  |  |  | 60 |  |
|  |  |  | C-4 |  |  |  |  |  |  | 60 |
|  |  | (C-II) | C-5 |  |  |  |  |  |  |  |
|  |  |  | C-6 |  |  |  |  |  |  |  |
|  | Inorganic ultrafine particles (D) (weight %) |  | D-1 |  |  |  |  |  |  |  |
|  |  |  | D-2 |  |  |  |  |  |  |  |
|  |  |  | D-3 |  |  |  |  |  |  |  |
| Transparency (ΔL) |  |  |  | 32 | 35 | 33 | 30 | 32 | 28 | 27 |
| Haze (%) |  |  |  | 96 | 70 | 85 | 96 | 96 | 97 | 96 |
| Total light transmittance (%) |  |  |  | 86 | 87 | 87 | 84 | 87 | 84 | 84 |
| Handling properties |  |  |  | 3 | 3 | 3 | 3 | 3 | 3 | 3 |
| Amount of consistency change (mm) |  |  |  | +0.8 | +0.7 | +0.7 | +0.4 | +0.2 | +0.9 | +0.3 |
| Flexural strength (MPa) |  |  |  | 131 | 133 | 133 | 132 | 136 | 127 | 132 |
| Polishability (%) |  |  |  | 80 | 82 | 82 | 80 | 77 | 84 | 78 |

TABLE 2

|  |  |  | Examples | | | | | | |
|---|---|---|---|---|---|---|---|---|---|
|  |  |  | 8 | 9 | 10 | 11 | 12 | 13 | 14 |
| Components of dental curable composition | Polymerizable monomer (A) (weight %) | A-1 |  |  |  | 20 | 20 | 20 |  |
|  |  | A-2 | 30 |  |  |  |  |  |  |
|  |  | A-3 |  | 30 |  |  |  |  |  |
|  |  | A-4 |  |  | 30 |  |  |  | 20 |
|  | Inorganic particles (B) (weight %) | B-1 | 5 | 5 | 5 |  |  |  | 5 |
|  |  | B-2 |  |  |  | 5 |  |  |  |
|  |  | B-3 |  |  |  |  | 5 |  |  |
|  |  | B-4 |  |  |  |  |  | 5 |  |

TABLE 2-continued

|  |  |  |  | Examples | | | | | | |
|---|---|---|---|---|---|---|---|---|---|---|
|  |  |  |  | 8 | 9 | 10 | 11 | 12 | 13 | 14 |
|  | Inorganic | (C-I) | C-1 | 65 | 65 | 65 | 75 | 75 | 75 |  |
|  | particles (C) |  | C-2 |  |  |  |  |  |  |  |
|  | (weight %) |  | C-3 |  |  |  |  |  |  | 15 |
|  |  |  | C-4 |  |  |  |  |  |  |  |
|  |  | (C-II) | C-5 |  |  |  |  |  |  | 60 |
|  |  |  | C-6 |  |  |  |  |  |  |  |
|  | Inorganic ultrafine |  | D-1 |  |  |  |  |  |  |  |
|  | particles (D) |  | D-2 |  |  |  |  |  |  |  |
|  | (weight %) |  | D-3 |  |  |  |  |  |  |  |
| Transparency (ΔL) |  |  |  | 30 | 27 | 28 | 32 | 31 | 34 | 30 |
| Haze (%) |  |  |  | 96 | 96 | 96 | 95 | 96 | 90 | 95 |
| Total light transmittance (%) |  |  |  | 84 | 87 | 87 | 87 | 86 | 88 | 85 |
| Handling properties |  |  |  | 3 | 3 | 3 | 3 | 3 | 3 | 4 |
| Amount of consistency change |  |  |  | +0.5 | +0.6 | +0.7 | +0.4 | +0.5 | +0.5 | +0.2 |
| Flexural strength (MPa) |  |  |  | 132 | 134 | 132 | 134 | 132 | 129 | 143 |
| Polishability (%) |  |  |  | 81 | 81 | 82 | 79 | 80 | 83 | 86 |

TABLE 3

|  |  |  |  | Examples | | | | | |
|---|---|---|---|---|---|---|---|---|---|
|  |  |  |  | 15 | 16 | 17 | 18 | 19 | 20 |
| Components of | Polymerizable |  | A-1 |  |  |  |  |  |  |
| dental curable | monomer (A) |  | A-2 |  |  |  |  |  |  |
| composition | (weight %) |  | A-3 |  |  |  |  |  |  |
|  |  |  | A-4 | 20 | 15 | 15 | 15 | 15 | 15 |
|  | Inorganic |  | B-1 | 5 | 5 | 5 | 5 | 5 | 5 |
|  | particles (B) |  | B-2 |  |  |  |  |  |  |
|  | (weight %) |  | B-3 |  |  |  |  |  |  |
|  |  |  | B-4 |  |  |  |  |  |  |
|  | Inorganic | (C-I) | C-1 |  |  |  |  |  |  |
|  | particles (C) |  | C-2 |  |  |  |  |  |  |
|  | (weight %) |  | C-3 | 60 | 50 | 30 | 25 | 25 | 25 |
|  |  |  | C-4 |  |  |  |  |  |  |
|  |  | (C-II) | C-5 |  | 30 | 50 | 50 | 50 | 50 |
|  |  |  | C-6 | 15 |  |  |  |  |  |
|  | Inorganic ultrafine |  | D-1 |  |  |  | 5 |  |  |
|  | particles (D) |  | D-2 |  |  |  |  | 5 |  |
|  | (weight %) |  | D-3 |  |  |  |  |  | 5 |
| Transparency (ΔL) |  |  |  | 27 | 31 | 32 | 30 | 31 | 29 |
| Haze (%) |  |  |  | 96 | 96 | 96 | 96 | 96 | 96 |
| Total light transmittance (%) |  |  |  | 86 | 85 | 84 | 84 | 84 | 84 |
| Handling properties |  |  |  | 4 | 4 | 4 | 5 | 5 | 5 |
| Amount of consistency change |  |  |  | −0.1 | +0.3 | +0.2 | −0.2 | −0.1 | +0.1 |
| Flexural strength (MPa) |  |  |  | 147 | 146 | 147 | 145 | 142 | 147 |
| Polishability (%) |  |  |  | 84 | 86 | 83 | 84 | 85 | 83 |

TABLE 4

|  |  |  |  | Examples | | | | | |
|---|---|---|---|---|---|---|---|---|---|
|  |  |  |  | 21 | 22 | 23 | 34 | 25 | 26 |
| Components of | Polymerizable |  | A-1 |  |  |  |  |  |  |
| dental curable | monomer (A) |  | A-2 |  |  |  |  |  |  |
| composition | (weight %) |  | A-3 |  |  |  |  |  |  |
|  |  |  | A-4 | 20 | 20 | 20 | 20 | 20 | 20 |
|  | Inorganic |  | B-1 | 0.5 | 10 |  |  |  |  |
|  | particles (B) |  | B-2 |  |  |  |  |  |  |
|  | (weight %) |  | B-3 |  |  |  |  |  |  |
|  |  |  | B-4 |  |  |  |  |  |  |
|  |  |  | B-6 |  |  | 1 | 5 | 8 |  |
|  |  |  | B-7 |  |  |  |  |  | 1 |
|  | Inorganic | (C-I) | C-1 |  |  |  |  |  |  |
|  | particles (C) |  | C-2 |  |  |  |  |  |  |
|  | (weight %) |  | C-3 | 60 | 50 | 50 | 50 | 50 | 50 |
|  |  |  | C-4 |  |  |  |  |  |  |

TABLE 4-continued

|  |  |  | Examples |  |  |  |  |  |
|---|---|---|---|---|---|---|---|---|
|  |  |  | 21 | 22 | 23 | 34 | 25 | 26 |
|  | (C-II) | C-5 |  | 20 |  |  |  |  |
|  |  | C-6 | 19.5 |  | 29 | 25 | 22 | 29 |
| Inorganic ultrafine | | D-1 | | | | | | |
| particles (D) | | D-2 | | | | | | |
| (weight %) | | D-3 | | | | | | |
| Transparency (ΔL) | | | 34 | 27 | 33 | 31 | 29 | 32 |
| Haze (%) | | | 74 | 97 | 75 | 90 | 95 | 71 |
| Total light transmittance (%) | | | 87 | 82 | 88 | 86 | 82 | 89 |
| Handling properties | | | 4 | 4 | 4 | 4 | 4 | 4 |
| Amount of consistency change | | | +0.2 | +0.3 | +0.2 | +0.3 | +0.3 | +0.4 |
| Flexural strength (MPa) | | | 143 | 146 | 141 | 142 | 138 | 139 |
| Polishability (%) | | | 84 | 83 | 82 | 81 | 82 | 84 |

TABLE 5

|  |  |  | Examples |  |  |  |  |  |
|---|---|---|---|---|---|---|---|---|
|  |  |  | 27 | 28 | 29 | 30 | 31 | 32 |
| Components of dental curable composition | Polymerizable monomer (A) (weight %) | A-1 | | | | | | |
| | | A-2 | | | | | | |
| | | A-3 | | | | | | |
| | | A-4 | 20 | 20 | 20 | 20 | 30 | 25 |
| | Inorganic particles (B) (weight %) | B-1 | | | | | | |
| | | B-2 | | | | | | |
| | | B-3 | | | | | | |
| | | B-4 | | | | | | |
| | | B-6 | | | 5 | 5 | 5 | 5 |
| | | B-7 | 5 | 7 | | | | |
| | Inorganic particles (C) (weight %) | (C-I) C-1 | | | | | | |
| | | C-2 | | | | | | |
| | | C-3 | 50 | 50 | 60 | 15 | 25 | 25 |
| | | C-4 | | | | | | |
| | | (C-II) C-5 | | | | | | |
| | | C-6 | 25 | 23 | 15 | 60 | 40 | 40 |
| | Inorganic ultrafine particles (D) (weight %) | D-1 | | | | | | 5 |
| | | D-2 | | | | | | |
| | | D-3 | | | | | | |
| Transparency (ΔL) | | | 29 | 26 | 30 | 28 | 28 | 30 |
| Haze (%) | | | 89 | 94 | 87 | 92 | 89 | 91 |
| Total light transmittance (%) | | | 84 | 81 | 82 | 80 | 83 | 82 |
| Handling properties | | | 4 | 4 | 4 | 4 | 4 | 5 |
| Amount of consistency change | | | +0.5 | +0.5 | +0.4 | +0.3 | +0.4 | +0.2 |
| Flexural strength (MPa) | | | 141 | 142 | 138 | 135 | 133 | 139 |
| Polishability (%) | | | 85 | 85 | 82 | 83 | 82 | 82 |

TABLE 6

|  |  |  | Comparative Examples |  |  |  |  |  |  |
|---|---|---|---|---|---|---|---|---|---|
|  |  |  | 1 | 2 | 3 | 4 | 5 | 6 | 7 |
| Components of dental curable composition | Polymerizable monomer (A) (weight %) | A-1 | 30 | 30 | 30 | 30 | 30 | 30 | |
| | | A-2 | | | | | | | |
| | | A-3 | | | | | | | |
| | | A-4 | | | | | | | |
| | (Monomer for comparison) | A-5 | | | | | | | 30 |
| | Inorganic particles (B) (weight %) | B-1 | | | | 15 | | 5 | 5 |
| | | B-2 | | | | | | | |
| | | B-3 | | | | | | | |
| | | B-4 | | | | | | | |
| | (Particles for comparison) | B-5 | | 5 | | | | | |
| | | C-5* | 5 | | | | | | |
| | Aggregated particles II (Particles for comparison) | | | | | | | 5 | |

TABLE 6-continued

|  |  |  | Comparative Examples | | | | | | |
|---|---|---|---|---|---|---|---|---|---|
|  |  |  | 1 | 2 | 3 | 4 | 5 | 6 | 7 |
| Inorganic particles (C) (weight %) | (C-I) | C-1 | 65 | 65 | 70 | 55 | 65 |  | 65 |
|  |  | C-2 |  |  |  |  |  |  |  |
|  |  | C-3 |  |  |  |  |  |  |  |
|  |  | C-4 |  |  |  |  |  |  |  |
|  | (C-II) | C-5 |  |  |  |  |  |  |  |
|  |  | C-6 |  |  |  |  |  |  |  |
| Aggregated particles I (Particles for comparison) |  |  |  |  |  |  |  | 65 |  |
| Inorganic ultrafine particles (D) (weight %) |  | D-1 |  |  |  |  |  |  |  |
|  |  | D-2 |  |  |  |  |  |  |  |
|  |  | D-3 |  |  |  |  |  |  |  |
| Transparency (ΔL) |  |  | 37 | 21 | 36 | 22 | 26 | 30 | 20 |
| Haze (%) |  |  | 32 | 89 | 31 | 96 | 57 | 92 | 88 |
| Total light transmittance (%) |  |  | 87 | 77 | 86 | 78 | 82 | 80 | 79 |
| Handling properties |  |  | 3 | 3 | 3 | 3 | 3 | 3 | 3 |
| Amount of consistency change |  |  | +0.7 | +0.6 | +0.7 | +0.4 | +1.6 | +1.8 | +0.9 |
| Flexural strength (MPa) |  |  | 134 | 135 | 132 | 131 | 128 | 130 | 121 |
| Polishability (%) |  |  | 82 | 61 | 83 | 82 | 80 | 78 | 82 |

*Inorganic particles C-5 were used instead of inorganic particles (B).

In all the compositions of Examples 1 to 32, high transparency and light diffusion were obtained. Furthermore, good paste handling properties also were obtained. As for the mechanical strength, polishability, and amount of consistency change, i.e., stability of paste properties, favorable results were obtained.

In Comparative Example 1, the inorganic particles C-5 were used instead of the inorganic particles (B). Since the refractive index of the inorganic particles C-5 was greater than the range of refractive indices of the inorganic particles (B) of the present invention, the refractive index of the polymerizable monomer (A) and that of the inorganic particles (C) were closer to each other. As a result, Comparative Example 1 was significantly inferior in light diffusion to Examples. The inorganic particles B-5 that were used in Comparative Example 2 were non-aggregated large particles having an average particle size of 1.7 μm. As a result, Comparative Example 2 was significantly inferior in polishability to Examples. In Comparative Example 3, the inorganic particles (B) were not used. As a result, Comparative Example 3 was significantly inferior in light diffusion to Examples. In Comparative Example 4, the content of the inorganic particles B-1 used therein was higher than the range of contents of the present invention. As a result, Comparative Example 4 was significantly inferior in transparency to Examples. The aggregated particles II that were used in Comparative Example 5 were composed of silica particles of 0.2 μm as primary particles. As a result, Comparative Example 5 was inferior in light diffusion to Examples, and had a greater amount of consistency change than Examples. In the aggregated particles I that were used in Comparative Example 6, the primary particles were loosely bonded with each other. As a result, Comparative Example 6 had a greater amount of consistency change. The polymerizable monomer (A) that was used in Comparative Example 7 had a lower refractive index after polymerization than the range of refractive indices of the present invention, with a larger difference from the refractive index of the inorganic particles (C). As a result, Comparative Example 7 was inferior in transparency.

Industrial Applicability

The dental curable composition of the present invention can be used suitably as a substitute for a part of a natural tooth or an entire natural tooth in the field of dental treatment.

The invention claimed is:

1. A dental curable composition comprising:
a polymerizable monomer (A) having a refractive index of 1.52 to 1.58 after polymerization;
inorganic particles (B) having a refractive index of 1.43 to 1.50; and
inorganic particles (C) having a refractive index of 1.52 to 1.58,
wherein the inorganic particles (B) are aggregates of inorganic fine particles having an average primary particle size of 2 to 50 nm, and the content of the inorganic particles (B) is 0.1 to 10% by weight,
and wherein the inorganic particles (C) comprise:
non-aggregated inorganic particles (C-I) having an average particle size of 0.1 to 1.0 μm, and
aggregated inorganic particles (C-II) having an average particle size of 1 to 20 μm and comprising silica-based fine particles having an average particle size of 2 to 50 nm and an oxide comprising at least one heavy metal where a weight ratio between the inorganic particles (C-I) and the inorganic particles (C-II) is 1:4 to 4:1.

2. The dental curable composition according to claim 1, wherein the inorganic particles (B) have an average particle size of 1.0 to 20 μm.

3. The dental curable composition according to claim 1, wherein the inorganic particles (B) have a specific surface area of 50 to 400 m²/g and a pore volume of 0.05 to 1.5 mL/g.

4. The dental curable composition according to claim 1, wherein a difference between the refractive index of the polymerizable monomer (A) after polymerization and the refractive index of the inorganic particles (C) is 0.03 or less.

5. The dental curable composition according to claim 1, wherein a difference between the refractive index of the polymerizable monomer (A) after polymerization and the refractive index of the inorganic particles (B) is 0.05 or more.

6. The dental curable composition according to claim 1, wherein the dental curable composition contains 8 to 40% by weight of the polymerizable monomer (A), 0.1 to 10% by weight of the inorganic particles (B), and 59.9 to 91.9% by weight of the inorganic particles (C).

7. The dental curable composition according to claim 1, further comprising 1 to 10% by weight of inorganic ultrafine particles (D) having an average particle size of 5 to 50 nm.

8. A composite resin comprising the dental curable composition according to claim 1.

9. The dental curable composition according to claim 1, wherein polymerizable monomer (A) has a refractive index of 1.53 to 1.58 after polymerization.

10. The dental curable composition according to claim 1, wherein polymerizable monomer (A) is a (meth)acrylic acid ester.

11. The dental curable composition according to claim 1, wherein:
   non-aggregated inorganic particles (C-I) have an average particle size of 0.2 to 0.7 μm, and
   aggregated inorganic particles (C-II) have an average particle size of 2.0 to 15 μm and comprise silica-based fine particles having an average particle size of 5 to 35 nm and an oxide comprising at least one heavy metal
   where the weight ratio between the inorganic particles (C-I) and the inorganic particles (C-II) is 1:3 to 3:1.

12. The dental curable composition according to claim 11, wherein said at least one heavy metal is at least one selected from the group consisting of Al, Ti, Zr, Sr, Ba, La, Y, and Yb.

13. The dental curable composition according to claim 11, wherein polymerizable monomer (A) has a refractive index of 1.53 to 1.58 after polymerization.

14. The dental curable composition according to claim 11, wherein polymerizable monomer (A) is a (meth)acrylic acid ester.

15. The dental curable composition according to claim 14, wherein the dental curable composition contains 8 to 40% by weight of the polymerizable monomer (A), 0.1 to 10% by weight of the inorganic particles (B), and 59.9 to 91.9% by weight of the inorganic particles (C).

16. The dental curable composition according to claim 15, wherein said at least one heavy metal is at least one selected from the group consisting of Al, Ti, Zr, Sr, Ba, La, Y, and Yb.

* * * * *